US00PP28167P3

(12) United States Plant Patent
Olesen

(10) Patent No.: US PP28,167 P3
(45) Date of Patent: Jul. 11, 2017

(54) COMPACT FLORIBUNDA ROSE PLANT NAMED 'POULPAL067'

(50) Latin Name: ***Rosa* hybrid**
Varietal Denomination: Poulpal067

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/756,266

(22) Filed: Aug. 20, 2015

(65) Prior Publication Data

US 2017/0055396 P1 Feb. 23, 2017

(51) Int. Cl.
*A01H 5/02* (2006.01)

(52) U.S. Cl.
USPC ..... Plt./145

(58) Field of Classification Search
USPC ..... Plt./141, 145
See application file for complete search history.

(56) References Cited

PUBLICATIONS

Poulsen Roser A/S "Palace-Perfection by Poulsen" Oct. 2012 (1 page).*

* cited by examiner

*Primary Examiner* — Susan McCormick Ewoldt

(57) ABSTRACT

A new garden rose plant of the compact floribunda class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal067'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulpal067', originated as a single seedling from the stated cross.

The new variety may be distinguished from its male pollen parent and female seed parent primarily by the following characteristics. The female pollen parent is very compact growing to 20 cm in height, while the new variety grows to 40 cm in height. The male pollen parent produces flowers singly or cluster of 3 flower buds per stem, while the new variety produces flowers in clusters of 5 to 10 flower buds.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal067' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulpal067' was selected in the spring of 2010 by the inventor as a single plant from the progeny of the aforementioned hybridization.

Asexual reproduction of 'Poulpal067' by traditional budding and rooted cuttings was first done by Mogens N. Olesen in the nursery in Fredensborg, Denmark in July, 2010. This initial and other subsequent asexual propagations conducted in controlled environments have demonstrated that the characteristics of 'Poulpal067' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal067'.

Specifically illustrated in FIG. 1 is an open flower, flower petals detached, cluster of open flowers on a branch, bare stem, compound leaf, reproductive flower parts, and sepals detached.

Figure 1:
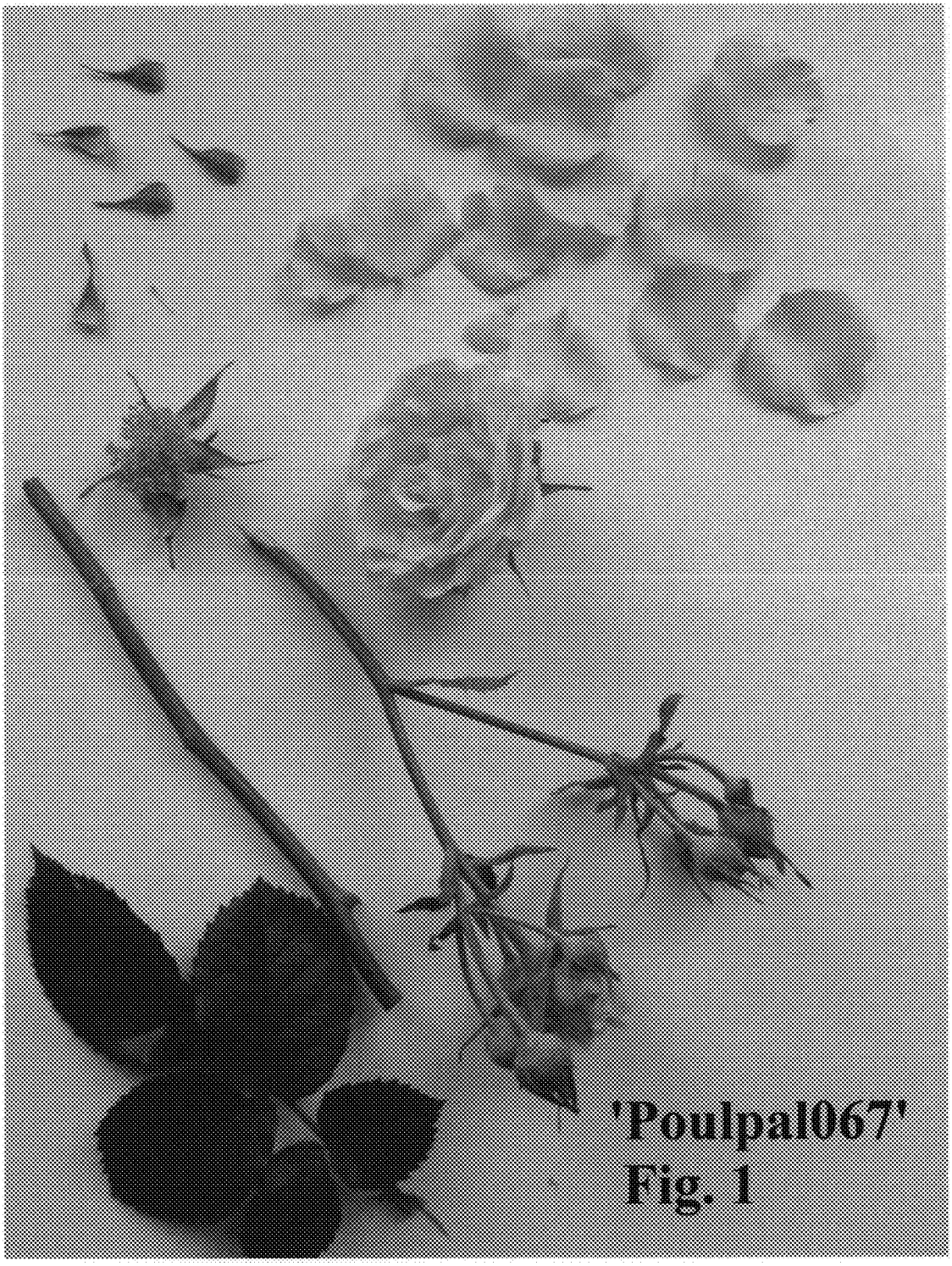
Figure 2:
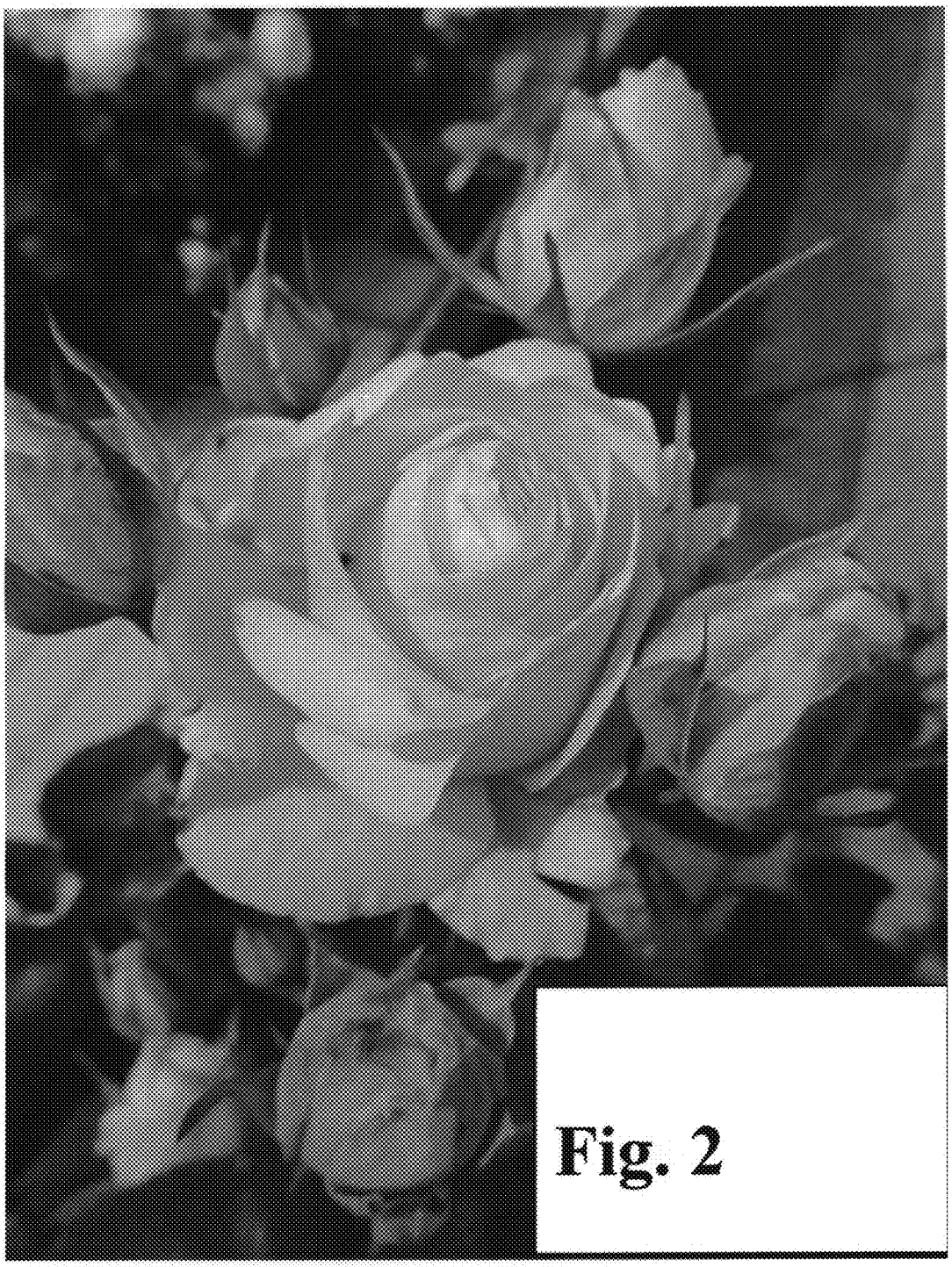

Specifically illustrated in FIG. 2 is a cluster of open flowers.

Plants shown are 1 year of age.

DETAILED DESCRIPTION OF THE VARIETY

The following is a description of 'Poulpal067', as observed in its growth in Odense Denmark. Observed plants are 1 year of age, and were grown on their own roots in 23 cm containers. Color references are made using The Royal Horticultural Society (London, England) Colour Chart, 2001, except where common terms of color are used.

For a comparison, several physical characteristics of the rose variety 'Poulsiana', U.S. Plant Pat. No. 11,638 are compared to 'Poulpal067' in Chart 1.

CHART 1

| | 'Poulpal067' | 'Poulsiana' |
|---|---|---|
| Petal Count | 45 | 15-20 |
| Flower Diameter | 70 mm | 55 to 60 mm |
| Flower petal upper surface upon opening | Yellow Group 6C | Yellow Group 7A |

Flower and Flower Bud

Blooming habit: Continuous.

Flower bud:

*Size.*—Upon opening, 28 mm in length from base of receptacle to end of bud. Bud diameter is 15 mm.

*Bud form.*—Urceolate.

*Bud color.*—As sepals divide petals are Yellow Group 2C.

*Sepal inner surface.*—Color: Yellow-Green Group 147C. Surface: Lightly pubescent.

*Sepal outer surface.*—Color: Yellow-Green Group 146D with intonations of Greyed-Purple Group 184B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—22 mm long, 8 mm wide.

*Receptacle.*—Texture: Smooth. Size: 6 mm in height, 10 mm wide. Color: Yellow-Green Group 144A. Shape: Funnel.

*Pedicel.*—Surface: Smooth. Length: 30 to 60 mm. Diameter: 3 mm on average. Color: Yellow-Green Group 144A. Strength: Moderate.

*Peduncle.*—Length: 4 to 6 cm. Diameter: About 4 mm. Color: Yellow-Green Group 146B. Texture: Smooth.

Flower bud development: Flower buds are borne in corymbs of 5 to 10 flower buds per stem. Corymbs are about 23 cm in diameter.

Flower bloom:

*Fragrance.*—Moderate floral scent.

*Duration.*—The blooms have a duration on the plant of approximately 15 days. Petals fall cleanly away from plant after flowers have fully matured.

*Size.*—Flower diameter is 70 mm when open. Flower depth is 30 mm.

*Flower shape.*—Rosette. Very double flower with many slightly overlapping petals of different sizes.

*Shape of flower, side view.*—The upper portion is flat. The lower portion is a flattened convex.

Petalage: Under normal conditions, flowers have 45 petals total, 10 of which are petaloids.

General tonality of flower: Open flowers are Yellow Group 12B. Tonality does not change.

Petal color: Upon opening, outer petals: Upper surface: Yellow-Green Group 6C. Lower surface: Yellow-Green Group 6D. Upon opening, inner petals: Upper surface: Yellow Group 10A. Lower surface: Yellow Group 10A. Basal petal spots: No distinctive coloration at the petal base observed. After opening, outer petals: Upper surface: Yellow Group 4B. Lower surface: Yellow Group 4C. After opening, inner petals: Upper surface: Yellow Group 6A. Lower surface: Yellow Group 6C. Basal petal spots: No distinctive coloration at the petal base observed.

Petals:

*Petal reflex.*—Weak.

*Margin.*—Entire with occasional cleft at the apex. Weak undulations.

*Shape.*—Generally ovate. Apex shape: Rounded. Base shape: Inner petals are acute, outer petals are obtuse.

*Size.*—40 mm (l)×30 mm (w).

*Texture.*—Smooth.

*Thickness.*—Average.

Petaloids:

*Size.*—15 mm (l) by 10 mm (w).

*Quantity.*—About 10.

*Shape.*—Irregular, asymmetric. The apex and base are acute.

*Color.*—Yellow Group 10A at upper and lower surface.

Reproductive flower parts:

*Pollen.*—None observed.

*Anthers.*—Size: 2 mm in length. Color: Yellow-Orange Group 23B. Quantity: 150 on average.

*Filaments.*—Color: Yellow-Orange Group 15A. Length: 5 mm.

*Pistils.*—Length: 4 mm. Quantity: 150 on average.

*Stigmas.*—Color: Yellow Group 4A.

*Styles.*—Color: Green-Yellow Group 1D.

*Location of stigmas.*—Level in location relative to the length of the filaments and the height of the anthers.

*Hips.*—None observed to date.

Plant

Plant growth: Upright, bushy. Plants are 40 cm in height, and 40 cm wide.

Stems:

*Color.*—Juvenile growth: Yellow-Green Group 146B with intonations of Greyed-Red Group 179B. Mature growth: Yellow-Green Group 146A with intonations of Greyed-Red Group 179B.

*Length.*—On average, canes are 35 cm from the base of the plant to the flowering portion.

*Diameter.*—6 mm.

*Internodes.*—On mature canes about 50 mm between nodes.

*Surface texture.*—Young wood: Smooth. Older wood: Smooth.

Long prickles: None observed.

Plant foliage:

*Compound leaf.*—150 mm (l)×150 (w).

*Quantity.*—2 leaves per 10 cm of stem on average.

*Leaf bearing angle to the stem.*—45 degrees.

*Color of mature foliage.*—Upper side: Yellow-Green Group 147A. Lower side: Yellow-Green Group 147C.

Plant leaves and leaflets:

*Stipules.*—Size: 20 mm long, 8 mm wide. Quantity: 2 per compound leaf. Shape: Linear, slightly broad based with outward extending apices. Margins: Finely serrated. Color: Yellow-Green Group 147A.

*Petiole*.—Length: 25 mm. Diameter: 2 mm. Upper surface: Color: Yellow-Green Group 146A with intonations of Greyed-Purple Group 187D. Lower surface: Color: Yellow-Green Group 144A.

*Rachis*.—Length: 20 mm. Upper surface: Color: Yellow-Green Group 146A with intonations of Greyed-Purple Group 187D. Lower surface: Color: Yellow-Green Group 144A.

*Leaflet*.—Quantity: Normally 5 leaflets. Margins: Serrulate. Size: On average terminal leaflets are 80 mm long, 60 mm wide. Shape: Generally ovate. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa,* downy mildew *Peronospora sparsa,* rust *Phragmidium* sps., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the compact floribunda rose class named 'Poulpal067', substantially as illustrated and described herein, due to its abundant yellow flowers, disease resistance, and extended period of bloom.

* * * * *

'Poulpal067'